United States Patent

Klopotek et al.

[11] 4,131,556
[45] Dec. 26, 1978

[54] METHOD FOR MANUFACTURING BROMINE AND BROMINE-IODINE DETERGENTS AND DISINFECTANTS

[75] Inventors: Alojzy Klopotek; Jerzy Uminski, both of Nowy Dwor Mazowiecki; Gabriela Dziala, Legionowo, all of Poland

[73] Assignee: Instytut Chemii Przemyslowej, Warsaw, Poland

[21] Appl. No.: 851,616

[22] Filed: Nov. 14, 1977

Related U.S. Application Data

[63] Continuation of Ser. No. 676,972, Apr. 14, 1976, which is a continuation-in-part of Ser. No. 439,755, Feb. 5, 1974, abandoned.

[30] Foreign Application Priority Data

Feb. 7, 1973 [PL] Poland ................................. 160631
Feb. 14, 1973 [PL] Poland ................................. 160732

[51] Int. Cl.² .......................... C11D 3/48; C11D 1/72
[52] U.S. Cl. ..................................... 252/106; 424/150; 568/609; 568/611; 568/614
[58] Field of Search ................... 252/106; 260/613 B, 260/615 B; 424/150, 127

[56] References Cited

U.S. PATENT DOCUMENTS

| | | |
|---|---|---|
| 2,863,798 | 12/1958 | Shelanski et al. ................. 424/150 |
| 2,868,686 | 1/1959 | Shelanski et al. ................. 424/150 |
| 2,931,777 | 5/1960 | Shelanski et al. ................. 252/106 |
| 3,028,299 | 4/1962 | Winicov et al. ................... 424/150 |
| 3,277,010 | 10/1966 | Schenck et al. ................... 252/106 |
| 3,285,816 | 11/1966 | Kaplan et al. .................... 424/150 |
| 3,367,877 | 2/1968 | Cantor et al. .................... 252/106 |

*Primary Examiner*—P.E. Willis, Jr.
*Attorney, Agent, or Firm*—Haseltine, Lake, & Waters

[57] ABSTRACT

A method for manufacturing bromine and bromine-iodine agents with detergent and disinfecting activity which comprises reacting a complex dibromineiodine ion $[IBr_2]^-$ or iodine bromide IBr with non-ionic surfactants, e.g. fatty alcohols extended with ethylene oxide, alkylphenols extended with ethylene oxide etc. When $[IBr_2]^-$-ion is used in the synthesis, a bromine complex compound corresponding to the general formula

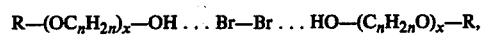

$$R-(OC_nH_{2n})_x-OH \ldots Br-Br \ldots HO-(C_nH_{2n}O)_x-R,$$

wherein R represents an alkyl, alkylamido, aryl or alkylaryl radical of 6–32 carbon atoms n is an integer from 2 to 4 and x is an integer representing the number of oxyalkylene groups and has a value from 2 to 50, is obtained.

When using an IBr compound in the synthesis, a bromine-iodine complex compound corresponding to the formula

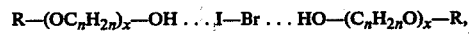

$$R-(OC_nH_{2n})_x-OH \ldots I-Br \ldots HO-(C_nH_{2n}O)_x-R,$$

wherein R, n and x have the meanings given above, is obtained.

The bromine-iodine complex compounds are stabilized additionally with bromides of alkali metals or alkaline earth metals.

On the basis of these compounds a wide range of efficient disinfectants and disinfectant detergents may be manufactured which can find application in medicine, veterinary medicine, agriculture, dairy and meat industries, etc.

13 Claims, No Drawings

METHOD FOR MANUFACTURING BROMINE AND BROMINE-IODINE DETERGENTS AND DISINFECTANTS

This is a continuation of application Ser. No. 676,972, filed Apr. 14, 1976 which is a continuation-in-part application of Ser. No. 439,755 filed Feb. 5, 1974, now abandoned.

This invention relates to a method for manufacturing bromine and bromine-iodine agents with detergent and disinfecting properties comprising bromine and bromine-iodine complex compounds with non-ionic surfactants. These agents are characterized by their bactericidal, fungicidal and virusocidal action, as well as by their detergency effects. They may be applied in the prophylaxis and therapy of mycoses, infectious and invasional diseases, as well as to washing and disinfecting in one operation of the equipment, installations and rooms in agriculture, food industry, medicine and veterinary medicine, municipal installations and transport.

Methods for manufacturing this class of complex compounds are not known. The closest art relates to agents with detergent and disinfecting properties prepared by reacting iodine with surfactants.

The methods for the preparation of such agents are described e.g. in British Pat. Nos. 962,955 and 2,977,315, in U.S. Pat. Nos. 2,931,777 and 3,028,299 and in German Pat. Nos. 1,171,112 and 1,642,088 and they consist in the preparation of mixtures of iodine or chlorine with detergents, in particular with non-ionic surfactants, with the optional addition of stabilizers of the acid type, mainly phosphoric and citric acids and alkali halides.

The main drawbacks of these known mixtures of iodine and chlorine with surfactants are their instability and their comparatively smooth decomposition with evolution of iodine or chlorine, which exerts a toxic action against warm-blooded organisms, causing irritation of skin and mucosae, as well as a strong corrosive effect on the surface of the washed and disinfected materials. The main reason for this instability is the fact that these mixtures are not stable, complex bonded compounds of the reactants, but they are only their loosely bonded mixtures. Attempts have been made to improve the stability of the above mentioned agents, e.g. of the iodophors according to the German Pat. No. 1,570,668 by giving them a special structure. The method consisted in lowering the rate of evolving free iodine by the agent by coating its surface with a liquid unsaturated monomer and then polymerizing it in the presence of a catalyst with formation of a sort of protective layer on the surface. The method is however troublesome and requires performing additional operations.

The scope of the present invention is the development of a method for manufacturing stable bromine and bromine-iodine agents having an efficient detergent and washing activity.

The method for manufacturing the bromine and bromine-iodine washing and disinfecting agents according to the invention is characterized by the fact that the synthesis of reactants gives a stable complex compound with no drawbacks of the hitherto known iodophors.

The stable bromine and bromine-iodine complex compounds with non-ionic surfactants are prepared in the synthesis of these compounds due to the application of iodine complex compounds with bromine instead of the hitherto used pure iodine.

The method according to the present invention comprises reacting a complex compound $[IBr_2]^-$ or IBr with non-ionic surfactants, e.g. fatty alcohols extended with ethylene oxide, alkylphenols extended with ethylene oxide, amides of fatty acids extended with ethylene oxide, etc.

When the $[IBr_2]^-$ is used in the synthesis, a bromine complex compound corresponding to the general formula

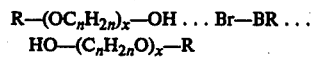
$HO$—$(C_nH_{2n}O)_x$—$R$ is obtained, wherein R represents an alkyl, alkylamido, aryl or alkylaryl radical of 6–32 carbon atoms, n is an integer from 2 to 4 and x is an integer from 2 to 50 and represents the number of oxyalkylene groups.

When IBr is used in the synthesis, a bromine-iodine complex compound corresponding to the general formula

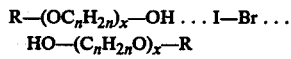
$HO$—$(C_nH_{2n}O)_x$—$R$ is obtained, wherein R, n and x have the meanings given above.

The course of the synthesis of the bromine complex compounds according to the present invention is, as follows:

To a saturated aqueous solution of an iodide of an alkali metal or of an alkaline earth metal, liquid bromine is added in the stoichiometric or nearly stoichiometric proportion at a temperature in the range of 0°–50° C. and with simultaneous stirring of the reaction mixture — in the reaction $I^- + Br_2 \rightarrow [Br_2]^-$. The prepared complex compound is added to a surfactant, which does not contain any water or only small amounts of water, in an amount of not more then 1 mole $[IBr_2]^-$ per 2 moles of non-ionic surfactant. This reaction is performed at a temperature not higher than 60° C. Because of the exothermic character of this reaction, the temperature must be controlled by the rate of addition of $[IBr_2]^-$ and by cooling the reaction vessels.

The course of the synthesis of the bromine-iodine complex compounds according to the present invention is, as follows:

In a reaction vessel stoichiometric amounts of iodine and bromine are mixed together at a temperature in the range of 0°–60° C., and the thus prepared iodine bromide is added to a non-ionic surfactant which does not contain any water or only small amounts of water, in an amount not more than 1 mole of iodine bromide per 2 moles of the non-ionic surfactant. This reaction is performed at a temperature not higher than 60° C. The temperature of the reaction mixture is controlled by the rate of addition of the iodine bromide and by cooling.

The bromine-iodine complex compounds with the non-ionic surfactants are stabilized additionally by addition of aqueous solutions of bromides of alkali metals or alkaline earth metals, the optimum stabilizing effect being obtained by addition of 1 mole of the bromides of the above mentioned metals per 1 mole of iodine bromide. The $Br^-$ ion formed in the aqueous solution prevents the decomposition of the complex compound.

The bromine and bromine-iodine complex compounds with non-ionic surfactants are prepared for direct application by dissolution in water with addition, if necessary, of the generally known agents increasing the bactericidal and detergency effectiveness, which are normally used in iodophors, such as e.g. organic acids, mineral acids, alkylarylsulfonic acids, alkylsulfonic acids, etc.

The method according to the present invention gives stable detergents and disinfectants with a strong bactericidal, fungicidal and virusocidal action together with high detergency effects, without any side-effects, which do not cause irritation and discoloration of skin, mucosae, and respiratory system and which are non-toxic to warm-blooded organisms. On the basis of these compounds a wide range of efficient disinfectants and disinfectant-detergents may be manufactured which can find application in medicine, veterinary medicine, agriculture, dairy, meat and brewing industries, winemaking, etc.

The following examples illustrate the subject of the present invention.

EXAMPLE I 2 kg potassium iodide are dissolved in 1.4 kg water. 1.93 kg liquid bromine are added dropwise to this solution at a temperature not higher than 60° C. The solution of iodine bromide prepared in this manner is introduced into a reactor fitted with a stirrer and containing 14.84 kg nonylphenol etherified with octaethylene glycol. The reaction mixture is cooled so that its temperature is not higher than 60° C.

In this reaction a liquid bromine-complex compound is obtained, which is soluble in water without signs of decomposition and to which auxiliary agents may be added, e.g. 1 kg sodium dodecylbenzenesulfonate and 2 kg orthophosphoric acid. The product thus obtained, according to its use, is diluted with water for direct application in a weight proportion of 1:5 to 1:200.

EXAMPLE II 2 kg iodine are mixed with 1.26 kg bromine at a temperature not higher than 60° C. The iodine bromide prepared in this manner is introduced into a reactor fitted with a stirrer and containing 16.74 kg stearyl alcohol etherified with octadecylethylene glycol. The reaction mixture is cooled so that its temperature is not higher than 60° C., with a simultaneous addition of 0.94 kg potassium bromide, as stabilizer.

In this reaction a bromine-iodine complex compound is obtained, which is soluble in water without signs of decomposition. As auxiliary agents 0.5 kg sodium dodecylbenzenesulfonate and 1 kg orthophosphoric acid are added.

The product thus obtained, according to its use, is diluted with water for direct application in a weight proportion from 1:5 to 1:200.

EXAMPLE III 1.8 kg sodium iodide are dissolved in 1.4 kg water. 1.93 kg liquid bromine are added dropwise to this solution, at a temperature during this chemical reaction not higher than 60° C.

The solution of iodine bromide prepared in this manner is introduced into a reactor fitted with a stirrer and containing 26.5 kg tallow alcohol etherified with 18 groups of ethylene oxide. The reaction mixture is cooled so that its temperature is not higher than 60° C., and 2.7 kg citric acid are added, as stabilizer.

The product thus obtained, according to its use, is diluted with water for direct application in a weight proportion from 1:5 to 1:200.

EXAMPLE IV 1.61 kg lithium iodide are dissolved in 1.3 kg water. 1.9 kg liquid bromine are added to this solution at a temperature during this chemical reaction not higher than 60° C.

The solution of iodine bromide prepared in this manner is introduced into a reactor fitted with a stirrer and containing 43.5 kg monoethanolamides of tallow acids extended with 35 groups of ethylene oxide. To this reaction mixture cooled to a temperature of 60° C., 12 kg of phosphoric acid are added.

The product thus obtained, according to its use, is diluted with water for direct application in a weight proportion from 1:5 to 1:200.

EXAMPLE V 2 kg iodine are mixed with 1.26 kg bromine at a temperature below 60° C.

The thus obtained iodine bromide is introduced into a reactor fitted with a stirrer and containing 9.1 kg nonylphenol extended with 8 moles of ethylene oxide. The reaction mixture is cooled so that its temperature is not higher than 60° C. with simultaneous addition of 0.81 kg sodium bromide, as stabilizer.

As an auxiliary agent 1.7 kg sodium dodecylbenzenesulfonate are added.

The product thus obtained, according to its use, is diluted with water for direct application in a weight proportion from 1:5 to 1:200.

EXAMPLE VI 2 kg iodine are mixed with 1.26 kg bromine at a temperature below 60° C.

The thus obtained iodine bromide is introduced into a reactor fitted with a stirrer and containing 28.4 kg monoethanolamides of tallow acids extended with 35 moles ethylene oxide. The reaction mixture is cooled so that its temperature is not higher than 60° C., with simultaneous addition of 0.69 kg lithium bromide, as stabilizer.

The product thus obtained, according to its use, is diluted with water for direct application in a weight proportion from 1:5 to 1:200.

EXAMPLE VII 3.26 kg iodine bromide are introduced into a reactor containing 17.3 kg β-naphthol oxyalkylenated with 13 moles propylene oxide of the formula $C_{10}H_7(OC_3H_6)_{13}$—OH; to stabilize the reaction mixture 1.05 kg magnesium bromide are added. The bromine-iodine complex compound of formula

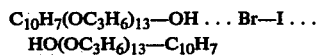

$$C_{10}H_7(OC_3H_6)_{13}-OH \ldots Br-I \ldots$$
$$HO(OC_3H_6)_{13}-C_{10}H_7$$

is obtained, which is soluble in water without any sign of decomposition. As an auxiliary agent 1.3 kg sodium dodecylbenzenesulfonate and 1.2 kg citric acid are added. The product thus obtained, according to its use, is diluted with water for direct application in a weight proportion of 1:5 to 1:200.

EXAMPLE VIII 3.26 kg. iodine bromide are introduced into a reactor containing 35.1 kg lauryl alcohol oxypropylenated with 20 moles propylene oxide of the formula $C_{12}H_{25}$—$(OC_3H_6)_{20}$—OH; to stabilize the reaction mixture 1.30 kg sodium bromide are added. The bromine-iodine complex compound of the formula

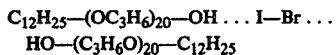

is obtained, which is soluble in water without any sign of decomposition. As auxiliary agents 13 kg tartaric acid and 3.2 kg sodium dodecylbenzenesulfonate are added. The product thus obtained, according to its use, is diluted with water for direct application in a weight proportion of 1:5 to 1:200.

EXAMPLE IX 2.06 kg iodine bromide are introduced into a reactor containing 19.8 kg stearyl alcohol etherified with 10 moles butylene oxide of the formula $C_{18}H_{37}$—$(C_4H_8O)_{10}$—OH; to stabilize the reaction mixture 1.09 kg potassium bromide are added. The bromine-iodine complex compound of the formula

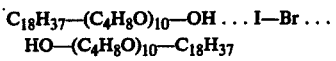

is obtained, which is soluble in water without any sign of decomposition. As auxiliary agents 0.5 kg sodium dodecylbenzenesulfonate and 1 kg orthophosphoric acid are added. The product thus obtained, according to its use, is diluted with water for direct application in a weight proportion of 1:5 to 1:200.

EXAMPLE X 0.166 kg potassium iodide are dissolved in 0.21 kg water, 0.16 kg liquid bromine are added dropwise to this solution at a temperature during this chemical reaction not higher than 60° C. The bromide-iodine solution prepared in this manner (having the formula $KIBr_2$) is introduced into a reactor fitted with a stirrer and containing 2.69 kg lauryl alcohol etherified with 20 groups of propylene oxide, of the formula: $C_{12}H_{25}$—$(OC_3H_6)_{20}$—OH.

The reaction mixture is cooled so that its temperature is not higher than 60° C.

The liquid bromine complex compound of the formula

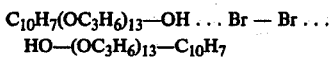

is obtained, which is soluble in water without any sign of decomposition.

As a auxiliary agent 0.1 kg sodium dodecylbenzenesulfate and 1.2 kg phosphoric acid are added.

The product thus obtained, according to its use, is diluted with water for direct application in a weight proportion of 1:5 to 1:200.

EXAMPLE XI 0.166 kg potassium iodide are dissolved in 0.21 kg water. 0.16 kg liquid bromine are added dropwise to this solution at a temperature during this chemical reaction, not higher than 60° C.

The bromide-iodine solution prepared in this manner (of formula $KIBr_2$) is introduced into a reactor fitted with a stirrer and containing 1.98 kg stearyl alcohol etherified with 10 groups of butylene oxide of the formula $C_{18}H_{37}$—$(C_4H_8O)_{10}$—OH.

The reaction mixture is cooled so that its temperature is not higher than 60° C.

The liquid bromine complex compound of the formula

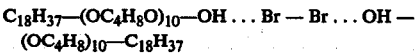

is obtained, which is soluble in water without any sign of decomposition.

As auxiliary agents 0.3 kg dodecyl benzenesulfate and 0.75 kg phosphoric acid are added.

The product thus obtained, according to its use, is diluted with water for direct application in a weight proportion of 1:5 to 1:200.

Table 1

| | Comparison between properties of substrates and products according to invention | | |
|---|---|---|---|
| Specification of the property | Substrates | | Characteristics of the product according to invention |
| | Name of | characteristics | |
| Action against skin of man and animals | Iodine bromide IBr | Caustic, causes slow-healing injuries of skin and its browning | No caustic and staining action; skin may be washed and disinfected with aqueous solution of the product without any detrimental effects |
| Action against mucosa | Iodine bromide | Strong caustic, suffocating and poisoning action | No vapors of IBr over the product and no caustic, suffocating and poisoning action |
| Action against metals and plastics | Iodine bromide | Strong corroding action | No corroding action against metals, except Ag |
| Water solubility | Iodine bromide | Water decomposes it with precipitation of metallic iodine | Soluble in water in any proportion without precipitation of metallic iodine |
| Color | Iodine bromide | Dark grey | Brown-orange |
| | Non-ionic surfactant | Colorless | |
| Quantitative way of joining the substrates | Iodine bromide plus non-ionic surfactant | In a strictly defined weight ratio, and not in an arbitrary ratio, as in a mixture | Not more than 1 mole IBr per 2 moles of surfactant. At ratios above 1:2, e.g. 1.1:2 metallic iodine precipitates |
| Changes in IR-spectra | Non-ionic surfactant | No changes in the spectrum in rela- | No changes in the position of character- |

Table 1-continued

Comparison between properties of substrates and products according to invention

| Specification of the property | Substrates — Name of | Substrates — characteristics | Characteristics of the product according to invention |
|---|---|---|---|
| | | tion to the product | istic absorption bands in relation to the substrate |
| Changes in NMR-spectrum | Non-ionic surfactant with OH-end-group blocked by $CH_3$-group | No changes in the spectrum in relation to the product comprising non-ionic surfactant with blocked OH-group plus iodine bromide | No changes in chemical shifts of signals of individual groups and in their appearance in relation to the spectrum of substrate - thus, the product is a mixture |
| Idem | Non-ionic surfactant without blocking of OH-group | Signal of proton in the image of OH-group has a typical appearance - it is low and broadened due to interchange | A substantial change in the appearance and in the values of chemical shifts of the proton of OH-group in relation to the substrate. A sharp signal of the proton of OH-group and its shifting to higher frequencies is observed; thus, the product is a chemical compound |

Table 2

Studies on determining the maximum molar ratio of iodine bromide bound by non-ionic surfactants

| NSF | Series I MR | Clear | ppt. | Series II MR | Clear | ppt. | Series III MR | Clear | ppt. | Series IV MR | Clear | ppt. |
|---|---|---|---|---|---|---|---|---|---|---|---|---|
| A | 0.9:2 | yes | no | 1:2 | yes | no | 1.1:2 | no | yes | 1.5:2 | no | yes |
| B | 0.9:2 | yes | no | 1:2 | yes | no | 1.1:2 | no | yes | 1.5:2 | no | yes |
| C | 0.9:2 | yes | no | 1:2 | yes | no | 1.1:2 | no | yes | 1.5:2 | no | yes |

Abbreviations and symbols:
MR — molar ratio
NSF — non-ionic surfactant
ppt. — precipitate of $I_2$
A — $C_9H_{19}$—$C_6H_4$—$(OC_2H_4)_8$—OH
B — $CH_3(CH_2)_{17}$—$(OC_2H_4)_{18}$—OH
C — $CH_3(CH_2)_{16}$—CONH—$(C_2H_4O)_{36}$—H A comparison of halogen content of the compounds of the prior art as illustrated by Kaplan et al U.S. Pat. No. 3,285,816, issued Nov. 15, 1966 and the corresponding products made according to the present invention is given in Table 3.

The method used to prepare the compounds of U.S. Pat. No. 3,285,816 is given in Examples 1b and 16 of said patent. Example 1b refers to the chlorine derivatives and Example 16 refers to the bromine derivatives.

The method of Example V was used to prepare the products according to the invention, using appropriate oxyethylenated phenols as starting materials. The percentages of halogen represent in maximum possible with the process of the invention.

Table 3

| Series | %I | %Br | %Cl | Kaplan |
|---|---|---|---|---|
| A-1 | 8.82 | 5.55 | | |
| A-2 | 21.56 | | 5.57 | Example 14a |
| A-3 | 20.40 | 9.73 | | Example 14b |
| B-1 | 2.87 | 1.81 | | |
| B-2 | 11.64 | | 3 | Example 11b |
| C-1 | 8.85 | 5.57 | | |
| C-2 | 21.34 | | 3 | Example 2b |

A — based on $C_9H_{19}$—$C_6H_4$—$(OC_2H_4)_9$—OH
B — based on $(C_9H_{19})_2$—$C_6H_3$—$(OC_2H_4)_{40}$—OH
C — based on $C_{12}H_{25}$—$C_6H_4$—$(OC_2H_4)_8$—OH

We claim:

1. A method for manufacturing a bromine complex of non-ionic detergent the formula of the complex being

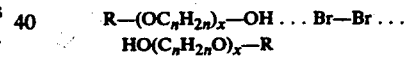

$$R—(OC_nH_{2n})_x—OH \ldots Br—Br \ldots HO(C_nH_{2n}O)_x—R$$

wherein R represents an alkyl, alkylamido, aryl or alkyaryl group having 6 to 32 carbon atoms, each x is an integer from 2 to 50 and represents the number of oxyalkylene groups and n is an integer from 2 to 4, comprising the step of reacting a solution containing $[IBr_2]^-$ ions with a non-ionic surfactant having the formula $R(OC_nH_{2n})_x$—OH, in which R, n and x are as defined above, in a proportion not exceeding 1 mole of $[IBr_2]^-$ ions per each 2 moles of non-ionic surfactant at a temperature in the range of 0°–60° C. under anhydrous or substantially anhydrous conditions to form the bromine complex of the non-ionic detergent.

2. The method of claim 1 wherein the $[IBr_2]^-$ ions are prepared by reacting bromine with an aqueous saturated solution of an iodide of an alkali metal or alkaline earth metal in substantially stoichiometric proportions at a temperature in the range of 0°–60° C.

3. The method of claim 1 wherein the non-ionic surfactant is nonylphenol etherified with 8 moles of ethylene oxide.

4. The method of claim 1 wherein the non-ionic surfactant is tallow alcohol etherified with 18 moles of ethylene oxide.

5. The method of claim 1 wherein the non-ionic surfactant is the monoethanol amide of tallow acid etherified with 35 moles of ethylene oxide.

6. The bromine complex obtained by the method of claim 1.

7. The method of claim 3 wherein the non-ionic surfactant is lauryl alcohol etherified with 20 groups of propylene oxide.

8. The method of claim 3 wherein the non-ionic surfactant is stearyl alcohol etherified with 10 groups of butylene oxide.

9. The bromine complex obtained by the method of claim 3.

10. The bromine complex obtained by the method of claim 4.

11. The bromine complex obtained by the method of claim 5.

12. The bromine complex obtained by the method of claim 6.

13. The bromine complex obtained by the method of claim 7.

* * * * *